United States Patent
Takahashi et al.

[11] 3,950,435
[45] Apr. 13, 1976

[54] HERBICIDAL DIPHENYL ETHERS

[75] Inventors: Ryohei Takahashi, Kusatsu; Kanichi Fujikawa, Kyoto; Isao Yokomichi, Kusatsu; Tadaaki Toki, Kusatsu; Shinzo Someya, Kusatsu, all of Japan

[73] Assignee: Ishihara Sangyo Kaisha Ltd., Osaka, Japan

[22] Filed: Mar. 25, 1975

[21] Appl. No.: 561,994

Related U.S. Application Data

[63] Continuation-in-part of Ser. No. 326,366, Jan. 24, 1973.

[30] Foreign Application Priority Data

| Jan. 27, 1972 | Japan | 47-10367 |
| May 13, 1972 | Japan | 47-47322 |
| Aug. 2, 1972 | Japan | 47-76944 |
| Dec. 6, 1972 | Japan | 47-121665 |
| Dec. 11, 1972 | Japan | 47-123369 |

[52] U.S. Cl. ............................... 260/613 R; 71/124
[51] Int. Cl.² ......................................... C07C 43/22
[58] Field of Search ................................ 260/613 R

[56] References Cited

UNITED STATES PATENTS

| 3,798,276 | 3/1974 | Bayer et al. | 260/612 R |
| 3,888,932 | 6/1975 | Bayer et al. | 260/612 R |

*Primary Examiner*—Bernard Helfin
*Attorney, Agent, or Firm*—Oblon, Fisher, Spivak, McClelland & Maier

[57] ABSTRACT

A herbicidal compund having the formula:

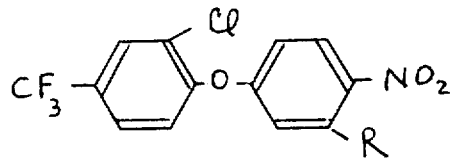

wherein R represents allyloxy or (2-propynyl) oxy group.

3 Claims, No Drawings

HERBICIDAL DIPHENYL ETHERS

CROSS-REFERENCE TO RELATED APPLICATIONS

This application is a continuation-in-part of U.S. application Ser. No. 326,366, filed Jan. 24, 1973.

BACKGROUND OF THE INVENTION

1. Field of the Invention

This invention relates to a class of herbicides which are effective for many agricultural uses.

2. Description of the Prior Art

Some diphenylether type herbicides such as 2,4-dichloro-4'-nitrodiphenyl ether, 2,4,6-trichloro-4'-nitrodiphenyl ether are known and have been practically used. In general, these herbicides have been considered to exhibit a more effective hrebicidal effect by application in paddy fields rather than in dry fields. Also, more effective use of the herbicide is realized by treating soil rather than the stems and leaves of plants.

This invention is concerned with a class of diphenylether type compounds which have excellent herbicidal properties. These diphenylether herbicides exhibit remarkable herbicidal properties which are improvements over the properties of known diphenylether herbicides. These improvements are as follows:

1. The herbicides exhibit a remarkable growth inhibition of barnyard-grass by treating the soil as well as the stems and leaves of the grass.
2. The herbicides exhibit excellent herbicidal properties against Sienedr spikerush, broad-leafed weeds, and the other various weeds.
3. The herbicides exhibit a remarkable genusselective growth controlling effect on gramineous plants.
4. The herbicides can effectively be applied at low concentrations in paddy fields as well as dry fields.

SUMMARY OF THE INVENTION

One object of this invention is to provide herbicides which have improved herbicidal properties.

Another object of this invention is to provide a class of diphenylether compounds which are useful as herbicides.

These objects and other objects of this invention as hereinafter will become apparent can be attained by providing a herbicide which contaninins at least one active ingredient having the formula

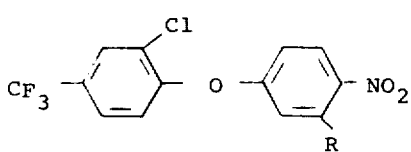

(I)

wherein R represents allyloxy or (2-propynyl)oxy group.

DETAILED DESCRIPTION OF THE PREFERRED EMBODIMENTS

The active ingredients of this invention can be prepared by the following process. 2-Chloro-4-trifluoromethyl diphenylether having the formula

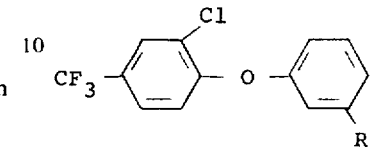

(II)

wherein R is as defined in formula (I) above, is reacted with a nitrating agent to substitute a nitro group in the 4'-position to produce compounds with the structure of formula (I). Also, the compounds of formula (I) can be obtained by substitution of the halogen atom of 3'-halogen-4'-nitro compounds in the presence of alkali with a corresponding allyl alcohol or (2-propynyl)alcohol.

2-Chloro-4-trifluoromethyl diphenylether with the formula (II) can be prepared by reacting 2-chloro-4-trifluoromethyl halobenzene having the formula

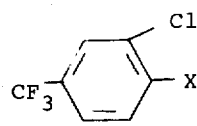

(III)

with a phenol having the formula

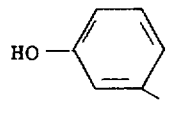

(IV)

wherein R is defined as in formula (I) above and X is a halogen atom in the presence of an alkaline compound. Suitable alkaline compounds useful for this reaction include an alkali metal hydroxide, or carbonate such as sodium hydroxide, sodium carbonate, potassium carbonate, and the like.

In the reaction of compound (III) with compound (IV) it is preferable to add a non-protonic polar solvent and a copper catalyst. Suitable solvents include dimethylsulfoxide, dimethylformamide, dimethylacetamide, N-methyl-pyrrolidone, hexamethyl phosphoramide or sulfolane. Suitable copper catalysts include copper powder, a copper-zinc mixture, cupric chloride, cuprous chloride, cupric oxide, cuprous oxide, cupric sulfate, cuprous bromide, and the like.

Generally, the reaction can be smoothly performed at temperatures higher than 100°C. If the reaction temperature is too high, disadvantageous side-reactions occur or the product obtained is colored. Accordingly, it is preferable to react the compounds at 130° - 200°C., especially 140° - 180°C.

An example of the preparation of active ingredient of this invention is illustrated and is not intended to be limiting unless otherwise specified.

PREPARATION

2-chloro-4-trifluoromethyo-3'-allyloxy-4'-nitrodiphenylether

A 2.0 g (0.006 mole) amount of 2,3'-dichloro-4-trifluoromethyl-4'-nitrodiphenylether; 1.32 g (0.023 mole) of allyl alcohol, 10 ml of dioxane and 0.4 g of potassium hydroxide were placed into a 50 ml four-necked flask equipped with a stirrer, a dropping funnel, a thermometer and a condenser. The flask was heated at 40° – 60°C, and the mixture was reacted for 6 hours with stirring. After the reaction, the contents of the flask were poured into a beaker filled with a suitable amount of water. The resulting product was extracted with ether. The ether phase was washed with water, hydrochloric acid and water, and was dried with calcium chloride. The solvent was removed to yield a crystalline product which was recrystallized from ethanol to yield 1.2 g of the product having a melting point of 55° – 60°C.

Having generally described the invention, a further understanding can be obtained by reference to certain specific examples which are provided herein for purposes of illustration only and are not intended to be limiting unless otherwise specified.

EXPERIMENT 1

Each pot of 1/10,000 are was filled with soil and the soil was supersaturated with water. A specific amount of air-dried edible barnyard grass seed was sown in the pot and covered with soil. When the barnyard grass appeared on the surface of the soil, water was poured into each pot to a depth of 3 cm and then an aqueous dispersion of one of the active ingredients of this invention was poured into the pot. Fourteen days after this treatment, the grass which had survived was cut, air dried and weighed. The results are shown in Table 1 in percent by weight of the grass which survived from the treated seed versus the untreated seed, and are indicated as "Degree of Growth".

EXPERIMENT 2

The procedure of Experiment 1 was followed except that water was poured to a depth of 4 cm at the two leaf stage of plant growth. Eighteen days after treatment with the specified ingredients, tests were made. The results are shown in Table II.

TABLE II

| Active Ingredient | (are = 100 m²) Degree of Growth (%) Amount of active ingredient (g/are) | | |
|---|---|---|---|
| | 20 | 10 | 5 |
| 2-chloro-4-trifluoromethyl-3'-allyloxy-4'-nitro diphenylether | 0 | 0 | 0 |
| 2-chloro-4-trifluoromethyl-3'-(2-propynyl)oxy-4'-nitro diphenylether | 0 | 0 | 0 |
| 2,4,6-trichloro-3'-methoxy-4'-nitro diphenylether | 88 | 97 | |
| 2-trifluoromethyl-4-chloro-3'-methoxy-4'-nitro diphenylether | 100 | 100 | |

EXPERIMENT 3

Each pot of 1/900 are was filled with soil and predetermined quantities of edible barnyard grass seeds were sown in the pots. The seeds were covered with soil which contained general upland weed seeds such as wild barnyard grass, bog stitch-wort, lawn grass, wavy bittercress, Polygonum species, large crabgrass, etc. to a depth of about 2 cm. Three days after sowing, a specific amount of an aqueous dispersion of each ingredient was sprayed onto the soil. Ten days after application of the ingredients, the growth condition of each of the plants and weeds was observed. The results are shown in Table III. In the Table, the degree of growth control is shown as it relates to the following standards:

5: Complete growth suppression is found
4: Remarkable growth suppression is found
3: Clear growth suppression compared with untreated plants is found
2: Slight growth suppression is found

TABLE 1

| Active Ingredient (m.p. or b.p.) | (are = 100 m²) Degree of Growth Amount of Active Ingredient (g/are) | |
|---|---|---|
| | 20 | 10 |
| 2-chloro-4-trifluoromethyl-3'-allyloxy-4'-nitro diphenylether (m.p. 55–60°C) | 0 | 0 |
| 2-chloro-4-trifluoromethyl-3'-(2-propynyl)oxy-4'-nitro diphenylether (b.p. 178–185°C/4mm Hg) | 0 | 0 |
| REFERENCE | | |
| 2-chloro-4-trifluoromethyl-3'-methoxy diphenyl ether | 73 | 85 |
| 2,2'-dichloro-4-trifluoromethyl diphenylether | 71 | 82 |
| 2-bromo-4-trifluoromethyl-3'-methoxy diphenylether | 65 | 94 |
| 2-chloro-4-trifluoromethyl-2'-methyl diphenylether | 85 | 97 |
| 2,6-dichloro-4-trifluoromethyl diphenyl ether | 75 | 92 |

1: No apparent difference between treated and untreated plants.

TABLE III

| Active Ingredient | Amount of active ingredient (g/are) | Degree of Growth Control (are = 100 m²) |||||||
|---|---|---|---|---|---|---|---|---|
| | | | | | Weed | | | |
| | | 1 | 2 | 3 | 4 | 5 | 6 | 7 |
| REFERENCE | | | | | | | | |
| 2-chloro-4-trifluoro-methyl-3'-allyloxy-4'-nitro diphenyl-ether | 100 | 5 | 5 | 5 | 5 | 5 | 5 | 5 |
| | 50 | 5 | 5 | 5 | 5 | 5 | 5 | 5 |
| | 20 | 5 | 5 | 5 | 5 | 5 | 5 | 5 |
| | 10 | 4 | 5 | 5 | 5 | 5 | 5 | 5 |
| 2-chloro-4-trifluoro-methyl-3'-(2-propynyl)oxy-4'-nitro diphenyl-ether | 100 | 5 | 5 | 5 | 5 | 5 | 5 | 5 |
| | 50 | 5 | 5 | 5 | 5 | 5 | 5 | 5 |
| | 20 | 4 | 5 | 5 | 5 | 5 | 5 | 5 |
| | 10 | 3 | 5 | 5 | 5 | 5 | 5 | 5 |

1. Edible barnyard grass
2. Wild barnyard grass
3. Bog stitch-wort
4. Lawn grass
5. Wavy bittercress
6. Large crabgrass

EXPERIMENT 4

Each pot of 1/5,000 are was filled with soil and predetermined amounts of edible barnyard grass seeds were sown and the seeds were covered with soil. When the barnyard grass had grown to the three leaf stage, a specific amount of an aqueous dispersion of each ingredient was sprayed onto the stems and leaves. Ten days after the application of the ingredients, the growth condition of the barnyard grass was observed. The results are shown in Table IV.

TABLE IV

| Active Ingredient | Degree of Growth Amount of Active Ingredient (g/are) (are — 100 m²) |||
|---|---|---|---|
| | 20 | 10 | 5 |
| 2-chloro-4-trifluoromethyl-3'-allyloxy-4'-nitro diphenylether | 5 | 5 | 5 |
| 2-chloro-4-trifluoromethyl-3'-(2-propynyl)oxy-4'-nitro diphenylether | 5 | 5 | 5 |

It is clear from the experimental tests that when the active ingredients of this invention are used as herbicides, the following advantages are found which makes their use suitable as herbicides.

1. They have remarkable high growth suppression effects against barnyard grass in paddy fields or in dry fields by application to the soil as well as by application to the stems and leaves of plants.
2. They have an excellent herbicidal affect on various weeds in paddy fields as well as in dry fields.
3. Excellent affects can be obtained in dry fields in low concentration.
4. The activity of the ingredients is high even when diluted, so that they can be applied in low concentrations.

The herbicides of this invention can be applied in various places such as paddy fields, dry lands, orchards, mulberry farms, forests, ridges, grounds, factory sites. Several suitable methods of application can be used which include application under flooded conditions, direct application to the soil or to the stems and leaves of plants. The herbicidal compounds can be applied in the form of an aqueous dispersion, a dust, a granule, a wettable powder, a water miscible solution or an emulsion with auxiliary agents such as a diluent, a solvent, an emulsifier and a spreader. The herbicidal compounds of this invention may be used together with other herbicidal compounds, insecticides, fungicides, fertilizers or soils.

The quantity of herbicide of this invention required depends upon the weather, soil, form of preparation of the agent, the season, method of application and type of weeds treated. Usually the active ingredients are applied in the range of 0.5 – 100 g/are, preferably 2.5 – 50 g/are.

| PREPARATION OF COMPOSITION 1 | |
|---|---|
| 2-chloro-4-trifluoromethyl-3'-allyloxy-4'-nitro diphenylether | 5 wt part |
| bentonite | 90 wt part |
| sodium lignin sulfonate | 5 wt part |

The components listed above were mixed and granulated with water to form the herbicidal composition (granules).

| PREPARATION OF COMPOSITION 2 | |
|---|---|
| 2-chloro-4-trifluoromethyl-3'-(2-propynyl)oxy-4'-nitro diphenylether | 40 wt part |
| kaoline powder | 55 wt part |
| sodium alkylbenzenesulfonate | 5 wt part |

The components listed above were uniformly mixed to form the herbicidal composition (wettable powder).

| PREPARATION OF COMPOSITION 3 | |
|---|---|
| 2-chloro-4-trifluoromethyl-3'-allyloxy-4'-nitro diphenylether | 15 wt part |
| polyoxyethylene stearate | 20 wt part |
| xylene | 65 wt part |

The components listed above were mixed to form a solution of the herbicide (emulsion type).

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. A herbicidal compound having the formula:

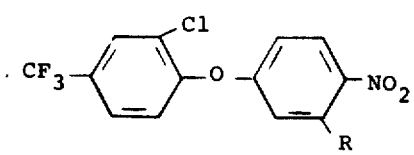

wherein R represents allyloxy or (2-propynyl)oxy group.

2. The herbicidal compound of claim 1, wherein R is allyloxy group.

3. The herbicidal compound of claim 1, wherein R is (2-propynyl)oxy group.

* * * * *